United States Patent [19]

Jakobson et al.

[11] Patent Number: 5,087,708
[45] Date of Patent: Feb. 11, 1992

[54] METHOD OF PREPARING 2,2-DIMETHYL-4-(2',3'-EPOXY) PROPOXYMETHYL-1,3-DIOXOLANE AND USE THEREOF

[75] Inventors: Gerald Jakobson; Werner Siemanowski, both of Rheinberg, Fed. Rep. of Germany

[73] Assignee: Deutsche Solvay-Werke GmbH, Solingen, Fed. Rep. of Germany

[21] Appl. No.: 673,334

[22] Filed: Mar. 22, 1991

[30] Foreign Application Priority Data

Mar. 27, 1990 [DE] Fed. Rep. of Germany ....... 4009739

[51] Int. Cl.$^5$ ................ C07D 317.22; C07D 317.10
[52] U.S. Cl. .................... 549/448; 549/430
[58] Field of Search .......................... 549/448

[56] References Cited

U.S. PATENT DOCUMENTS

| | | | |
|---|---|---|---|
| 3,978,087 | 8/1976 | Renner et al. | 549/448 |
| 3,978,088 | 8/1976 | Renner et al. | 549/448 |
| 4,060,532 | 11/1977 | Hartmann | 549/525 |
| 4,769,497 | 9/1988 | Messina et al. | 549/448 |
| 4,810,806 | 3/1989 | Krespan | 549/448 |

FOREIGN PATENT DOCUMENTS

| | | | |
|---|---|---|---|
| 2479822 | 10/1981 | France | 549/448 |
| 205277 | 9/1986 | Japan | 549/448 |

Primary Examiner—J. E. Evans
Attorney, Agent, or Firm—Foley & Lardner

[57] ABSTRACT

A method of making 2,2-dimethyl-4-(2',3'-epoxy)-propoxymethyl-1,3-dioxolane is disclosed, wherein isopropylidene glycerol and epichlorohydrin are reacted in a molar ratio of 0.7:1.0 to 1.0:0.7, respectively, in the presence of at least one Lewis acid or at least one strong inorganic acid at temperatures 283° K. to 373° K., and the initially formed isopropylidene glycerol chlorohydrin ether is reacted with a strongly alkaline base in a molar ratio of chlorohydrin ether to the alkaline base of 1.0:1.0 to 1.0:1.1, respectively, to givbe the 2,2-dimethyl-4-(2',3'-epoxy)propoxymethyl-1,3-dioxolane. This compound is suitable for use as an intermediate for the production of nonionic and/or ionic surfactants, as a reactive diluent and as an auxiliary solvent and auxiliary stabilizer.

6 Claims, No Drawings

METHOD OF PREPARING 2,2-DIMETHYL-4-(2',3'-EPOXY) PROPOXYMETHYL-1,3-DIOXOLANE AND USE THEREOF

BACKGROUND OF THE INVENTION

1. Field of the Invention

The present invention relates to a method of preparing 2,2-dimethyl-4-(2',3'-epoxy)propoxymethyl-1,3-dioxolane by reacting epichlorohydrin with isopropylidene glycerol using a catalyst and to uses of the compound prepared by the method.

2. Description of the Prior Art

A method of preparing 2,2-dimethyl-4-(2',3'-epoxy)-propoxymethyl-1,3-dioxolane is disclosed in DE-OS 3,220,035, in which acetone glycerol ketal (isopropylidene glycerol) is reacted together with epichlorohydrin in the presence of hexane and a phase transfer catalyst (trimethyldodecylammonium chloride). Disadvantages of this method relate to the requirements of using a solvent (e.g. hexane), approximately 3 molar excess of sodium hydroxide solution (based on acetone glycerol ketal), and approximately two-fold excess of epichlorohydrin for the reaction. Reaction procedures and control are difficult due to the strongly exothermic nature of the reaction. Moreover, additional operations are necessary due to the co-use of a solvent.

SUMMARY OF THE INVENTION

The present invention overcomes the problems and disadvantages of the prior art by providing a novel method for preparing 2,2-dimethyl-4-(2',3'-epoxy)propoxymethyl-1,3-dioxolane. The present invention represents a vast improvement and a novel approach for satisfying and meeting the needs, requirements and criteria for effective and useful manufacture and production of 2,2-dimethyl-4-(2',3'-epoxy)propoxymethyl-1,3-dioxolane in a safe and efficient manner.

The object of the present invention is to provide a method of preparing 2,2-dimethyl-4-(2',3'-epoxy)-propoxymethyl-1,3-dioxolane.

Another object of the invention is to provide uses of the compound made according to the method of the present invention.

Additional objects and advantages of the present invention will be set forth, in part, in the description which follows and, in part, will be obvious from the description or may be learned by practice of the invention. The objects and advantages of the invention may be learned by and attained by means of the instrumentalities and combination of steps particularly pointed out in the appending claims.

To achieve the foregoing objects and in accordance with the purpose of the present invention, as embodied and broadly described herein, the method of making 2,2-dimethyl-4-(2',3'-epoxy)propoxymethyl-1,3-dioxolane according to the present invention comprises a first step of producing isopropylidene glycerol chlorohydrin ether by reacting epichlorohydrin and isopropylidene glycerol using a catalyst at a temperature range from 283° K. to 373° K. in a reactor vessel and a second step of reacting the isopropylidene glycerol chlorohydrin ether and an alkaline base, wherein the catalyst is selected from the group consisting of Lewis acids and inorganic acids, the molar ratio between the epichlorohydrin and isopropylidene glycerol is between approximately 0.7:1.0 to 1.0:0.7, respectively, and the molar ratio between the isopropylidene glycerol chlorohydrin ether and the alkaline base is between approximately 1.0:1.0 to 1.0:1.1, respectively.

An alternate embodiment of the method of the present invention further comprises a distillation step immediately after the first step of producing isopropylidene glycerol chlorohydrin ether to remove unreacted epichlorohydrin and/or isopropylidene glycerol. Preferably, the distillation step is conducted at a temperature above 300° K., and more preferably between about 300° K. and 430° K. and under reduced pressure. In a modified embodiment, the distillate from the distillation step containing unreacted epichlorohydrin and/or isopropylidene glycerol is collected and returned to the reactor vessel for further reaction to produce isopropylidene glycerol chlorohydrin ether.

In further accordance with the objects and purpose of the present invention, uses for 2,2-dimethyl-4-(2',3'-epoxy)propoxymethyl-1,3-dioxolane made in accordance with the method of the present invention include use as an intermediate for the preparation of nonionic and/or ionic surfactants, use as a reactive diluent preferably for lacquers and paints, use as an auxiliary solvent for organic chemical compounds, and use as an auxiliary stabilizer for organic chemical compounds.

DETAILED DESCRIPTION OF THE PREFERRED EMBODIMENTS

According to the present invention, it has been discovered that a method for preparing 2,2-dimethyl-4-(2',3'-epoxy)propoxymethyl-1,3-dioxolane by reaction of epichlorohydrin with isopropylidene glycerol using a catalyst meets the aims and objects of the present invention when epichlorohydrin and isopropylidene glycerol are reacted in a molar ratio of 0.7:1 to 1:0.7, preferably 0.8:1 to 1:0.8, in the presence of at least one Lewis acid, preferably $BF_3$-etherate, $BF_3$-acetic acid and/or tin tetrachloride, and/or in the presence of at least one strong inorganic acid at temperatures ranging from about 283° K. to 373° K., and the resultant isopropylidene glycerol chlorohydrin ether is subsequently reacted with at least one strongly alkaline base, preferably sodium hydroxide solution, in a molar ratio of chlorohydrin ether to the strongly alkaline base (calculated without a water content) of 1.0:1.0 to 1.0:1.1, preferably 1.0:1.005 to 1.0:1.05, to give 2,2-dimethyl-4-(2',3'-epoxy)propoxymethyl-1,3-dioxolane.

According to a preferred embodiment of the present invention, after the reaction to produce isopropylidene glycerol chlorohydrin ether, unreacted epichlorohydrin and/or isopropylidene glycerol is removed by distillation at temperatures above 300° K., preferably at a temperature range from 300° K. to 430° K., under reduced pressure, and fed back into circulation for further reaction.

According to another preferred embodiment of the present invention, before distillation of unreacted epichlorohydrin and/or isopropylidene glycerol, the Lewis acid(s) and/or strong inorganic acid(s) are neutralized by at least one alkaline agent.

By the method of the present invention, there is provided a simple reaction procedure that proceeds under highly controllable conditions, that can be utilized for large scale production, and which avoids the use of organic chemical solvents. Moreover, the amount of reactants, hitherto used in considerable excess, based on isopropylidene glycerol, can be considerably reduced.

The present invention also relates to the use of 2,2-dimethyl-4-(2',3'-epoxy)propoxymethyl-1,3dioxolane as an intermediate for the preparation of nonionic and/or ionic surfactants.

The present invention also relates to the use of 2,2-dimethyl-4-(2',3'-epoxy)propoxymethyl-1,3-dioxolane as a reactive diluent, preferably for lacquers, wood preservatives, dyes and paints and also for plastics, for example plastisols, and as processing auxiliaries for plastics.

The present invention further relates to the use of 2,2-dimethyl-4-(2',3'-epoxy)propoxymethyl-1,3-dioxolane as an auxiliary, solvent and/or stabilizer for organic chemical compounds.

EXAMPLE 793 g (6 mol) of isopropylidene glycerol are added to a 2 liter double-jacket reactor (heating fluid: heat transfer oil; reaction in an inert gas atmosphere). 0.57 mol of boron trifluoride etherate is pipetted in with stirring and the reactor contents are heated to about 318° K. 5 mol of epichlorohydrin are then metered in over the course of about 1.5 hours at a maximum temperature of about 333° K. (preferably with cooling of the heat transfer oil). After a further 30 min, the reaction mixture is neutralized by the addition of 50% strength sodium hydroxide solution, and unreacted portions of starting materials are removed in vacuo by distillation.

1.05 mol of sodium hydroxide (as a 20% strength aqueous solution) per mol of hydrolyzable chlorine is added to the crude isopropylidene glycerol chlorohydrin ether, which is not further purified, and the resultant two-phase system is thoroughly mixed at about 323° K. by vigorous stirring. After complete conversion to the glycidyl ether (thin layer chromatographic checking), the aqueous phase is removed and the organic phase is subjected to fine distillation. 858 g (about 80% of theory) of 2,2-dimethyl-4-(2',3'-epoxy)propoxymethyl-1,3-dioxolane is obtained as the main fraction.

It will be apparent to those skilled in the art that various modifications and variations can be made in the method and use of the present invention without departing from the scope or spirit of the invention. It is intended that the present invention cover such modifications and variations of this invention provided they come within the scope of the appended claims and their equivalents.

What is claimed is:

1. A method of making 2,2-dimethyl-4-(2',3'-epoxy)-propoxymethyl-1,3-dioxolane comprising:
   a first step of producing isopropylidene glycerol chlorohydrin ether by reacting epichlorohydrin and isopropylidene glycerol using a catalyst at a temperature range from 283° K. to 373° K. in a reactor vessel,
   and a second step of reacting the isopropylidene glycerol chlorohydrin ether and an alkaline base, wherein
   the catalyst is selected from the group consisting of Lewis acids and inorganic acids,
   the molar ratio between the epichlorohydrin and isopropylidene glycerol is between approximately 0.7:1.0 to 1.0:0.7, respectively, and
   the molar ratio between the isopropylidene glycerol chlorohydrin ether and the alkaline base is between approximately 1.0:1.0 to 1.0:1.1, respectively.

2. The method as claimed in claim 1, further comprising a distillation step immediately after the first step of producing isopropylidene glycerol chlorohydrin ether to remove a distillate containing unreacted epichlorohydrin and/or isopropylidene glycerol 3. The method as claimed in claim 2, wherein the distillation step is conducted at a temperature above 300° K.

4. The method as claimed in claim 2, wherein the distillation step is conducted at a temperature between about 300° K. and 430° K. and under reduced pressure.

5. The method as claimed in claim 2, wherein the distillate containing unreacted epichlorohydrin and/or isopropylidene glycerol is collected and returned to the reactor vessel for further reaction to produce isopropylidene glycerol chlorohydrin ether.

6. The method as claimed in claim 2, wherein the catalyst is neutralized by at least one alkaline agent before the distillation step.

* * * * *